United States Patent [19]
Cassaday

[11] Patent Number: 5,192,504
[45] Date of Patent: Mar. 9, 1993

[54] FLUSHABLE LOW CARRYOVER CONTAINER

[75] Inventor: Michael M. Cassaday, Valhalla, N.Y.

[73] Assignee: Technicon Instruments Corporation, Tarrytown, N.Y.

[21] Appl. No.: 387,267

[22] Filed: Jul. 28, 1989

Related U.S. Application Data

[63] Continuation of Ser. No. 9,424, Feb. 2, 1987, abandoned, which is a continuation of Ser. No. 721,919, Apr. 11, 1985, abandoned.

[51] Int. Cl.$^5$ ............................................. G01N 21/05
[52] U.S. Cl. ........................................ 422/64; 422/81; 422/82; 422/102; 436/52; 436/53; 356/72; 356/73
[58] Field of Search ................. 422/64, 81, 82, 102, 422/100, 101; 436/52, 53, 177, 178, 180; 356/39, 72-73

[56] References Cited

U.S. PATENT DOCUMENTS

| | | | |
|---|---|---|---|
| 3,479,141 | 11/1969 | Smythe et al. | 436/53 |
| 3,989,381 | 11/1976 | Fulwyler | 356/39 |
| 3,990,849 | 11/1976 | Lee et al. | 436/177 X |
| 3,998,591 | 12/1976 | Eckfeldt | 422/68 |
| 4,102,368 | 7/1978 | Malfurt et al. | 422/64 X |
| 4,253,846 | 3/1981 | Smythe et al. | 422/82 X |
| 4,348,107 | 9/1982 | Leif | 356/72 |
| 4,471,297 | 9/1984 | Berg | 422/64 X |
| 4,515,274 | 5/1985 | Hollinger et al. | 356/39 X |

Primary Examiner—Robert J. Warden
Assistant Examiner—Lynn M. Kummert
Attorney, Agent, or Firm—Jeffrey M. Greenman; James J. Romano, Jr.

[57] ABSTRACT

Minimum carryover container for the successive containment of discrete liquids as are successively introduced thereinto, and minimum carryover discrete liquid analysis system utilizing the container, are disclosed; and operate through use of container materials which are selectively wettable by an immiscible isolation liquid which is introduced to the container independently of the discrete liquids to form an independently flowing isolation liquid stream which covers the walls of the container from the container inlet to the container outlet thereby preventing contact by the discrete liquids with the container walls. The container can include wall portions enabling the transmission of light energy therethrough from the outside of the container. The analysis system makes use of the container for the successive containment and processing for analysis of the discrete liquids; and for the generation and supply of an isolation liquid based discrete liquid stream containing the processed discrete liquids in series to analysis apparatus, the successive supply of the processed discrete liquids in series to anlysis apparatus by the successive withdrawal thereof from the container, or the successive analyses of the processed discrete liquids in situ in the container, respectively.

41 Claims, 8 Drawing Sheets

FLUSHABLE LOW CARRYOVER CONTAINER

This is a continuation of application Ser. No. 07/009,424 filed Feb. 2, 1987 by Mr. Michael M. Cassaday and assigned to the assignee hereof, now abandoned, which was in turn a continuation of application Ser. No. 06/721,919 filed Apr. 11, 1985 by Mr. Cassaday and assigned to the assignee hereof, now also abandoned.

BACKGROUND OF THE INVENTION

1. Field of The Invention

This invention relates to a new and improved minimum carryover container, and to a new and improved automated analysis system incorporating that container; both of which are particularly adapted for use in the automated successive analyses of a series of discrete sample liquids.

2. Description of the Prior Art

Although a wide variety of containers are, of course, known in the prior art, none are known which are configured or operable in the manner taught by this invention; or which can provide the particularly significant advantages of simplicity, low cost, absolute reliability, versatility of application, virtually limitless re-usability, and mimimization of carryover as are respectively provided by the container of this invention.

More specifically, although the reaction container or cuvette disclosed in U.S. Pat. No. 4,357,301 issued Nov. 2, 1982 to Michael M. Cassaday, et al, and ass to the assignee hereof, does function to provide a situs for the reaction of an aqueous sample liquid, and a reagent liquid, and does provide for the in situ colorimetric analysis of the duly reacted sample liquid; this container, being, either disposable or in no practical manner re-usable without the most thorough of washing (not disclosed), is clearly not directed as such to the minimization of sample liquid carryover. To the contrary, this container which is specifically disclosed as comprising a *hydrophilic* bottom surface having ridges or the like projecting upwardly therefrom, is designed to insure that an encapsulating film of an immiscible liquid as may surround a sample liquid segment dispensed into the container, is broken upon striking the bottom of the container to in turn insure sample and reagent liquid mixing and reaction within the container. As a result, contamination of the container by the sample liquid becomes a virtual certainty.

In like manner, although a number of automated, successive sample liquid analysis systems are known in the prior art which are made relevant to that of this invention by the disclosure of the use an immiscible isolation liquid to reduce sample liquid carryover through the generation of an isolation liquid based sample liquid stream, none are known which are configured or operable in the manner taught by this invention; or which can provide the particularly significant advantages of analysis system simplification, reduced costs in terms of both system fabrication and system operation, increased reliability, increased speed of operation, and increased sample liquid analysis accuracy as are respectively provided by the sample liquid analysis system of this invention.

More specifically, although the sample liquid analysis system disclosed in U.S. Pat. No. 3,479,141 issued Nov. 18, 1969 to W. J. Smythe, et al, and assigned to the assignee hereof, does operate satisfactorily to reduce sample liquid carryover through the generation of an immiscible isolation liquid based sample liquid stream; the means by which that stream is generated and the means by which the requisite sample liquid reagents and the like are added thereto in the requisite precise proportion(s), including the sample and recipient sides of a dialyzer, multi-tube peristaltic pumps, and conduit junctures and the like, are clearly more complex and costly, and less reliable than those of this invention, and are clearly less effective in reducing sample liquid carryover since the isolation liquid based sample liquid stream is only generated intermediate the sample analysis process. Too, the inherent limitations in peristaltic pump speed and dialysis rates limit the speed of operation of this analysis system in terms of sample liquid analyses per unit time to a number far below that which can be provided by the analysis system of this invention. In addition, the isolation liquid consumption rate of this system is much higher than that of the system of this invention, thus adding significantly to costs of system operation because appropriate isolation liquids are costly; while the inclusion of a dialyzer in this prior art analysis system significantly limits the versatility thereof in terms of the types of automated sample liquid analyses which can be performed thereby.

Similarly, although the sample liquid analysis system disclosed in U.S. Pat. No. 4,253,846 issued Mar. 3, 1981 to W. J. Smythe, et al, and assigned to the assignee hereof, also operates satisfactorily to reduce sample liquid carryover through the generation of an immiscible isolation liquid based sample liquid stream; the means by which that stream is generated and the means by which the requisite sample liquid reagents and the like are added thereto in the requisite precise proportion(s), including non-illustrated applicator means operatively associated with the sample liquid aspirating probe, and a complex assembly of poppet valve injectors and equally complex operatively associated actuating structures, are again clearly more complex and costly, and less reliable than those of this invention. In addition, the requirement for successive sample and reagent liquid introduction into the sample liquid stream inherently limits the speed of operation of this prior art analysis system in terms of the number of sample liquid analyses per unit time to a number far below that which can be provided by the analysis system of this invention.

Similarly, although the sample analysis system disclosed in currently pending application for U.S. patent of S. Saros, et al, Ser. No. 441,181 filed Nov. 11, 1982 and assigned to the assignee hereof, also operates satisfactorily to reduce sample liquid carryover through the generation of an isolation liquid based sample liquid stream, the means by which that stream is generated and the means by which the requisite sample liquid reagents and the like are added thereto in the requisite precise proportion(s), including an applicator shroud operatively associated with the sample and reagent liquids aspirating probe, and a complex sample-reagent liquids metering assembly requiring photodectors and stop valves and operatively associated operating structure, are again clearly more complex and costly, and far less reliable than those of this invention. In addition, the requirement for successive sample and reagent liquid aspiration and introduction into the sample liquid stream at the stream formation or "front end" of this prior art analysis system again inherently limits the speed of operation in terms of the number of sample liquid analyses which can be performed per unit time to a number far below that which can be provided by the analysis system of this invention.

Of course, the specified disadvantages with regard to high cost of each of the prior art analysis systems of U.S. Pat. Nos. 3,479,141 and 4,253,846, and the analysis system of currently pending application for U.S. patent Ser. No. 441,181 would, in each instance, virtually preclude the economically realistic paralleling thereof for use in multi channel analysis systems.

U.S. Pat. Nos. 4,357,301, 3,479,141 and 4,253,846, and currently pending application for U.S. patent Ser. No. 441,181, now indicated as containing allowable subject matter, are hereby incorporated by reference in this application.

SUMMARY OF THE INVENTION

This invention relates to a minimum carryover container, and to an automated analysis system incorporating the container. The container comprises a bore having inlet means for the successive introduction of discrete liquids thereinto by operatively associated discrete liquid introduction means, and outlet means for the successive flow of the discrete liquids from the container bore. Means independent of the discrete liquid introduction means are included in the container and are operable to introduce an isolation liquid to the container bore inlet inlet means to cover the container bore walls from the inlet means to the outlet means with an independently flowing stream of the isolation liquid. The isolation liquid is immiscible with the discrete liquids, and the container bore walls are selectively wettable by the isolation liquid to the substantial exclusion of the discrete liquids to substantially prevent contact by the discrete liquids with the container bore walls and thus minimize discrete liquid carryover, e.g. the contamination of a succeeding discrete liquid by the residue of a preceding discrete liquid, attendant the successive containment of the discrete liquids in the container bore. The container bore walls can contain aligned sections which are substantially transmittive of light energy from without the container.

The analysis system makes use of the container for the successive containment and processing for analysis of the discrete liquids and, to that effect, includes means to successively introduce the discrete liquids into the container bore which are only operable to introduce a succeeding discrete liquid into the container bore after a preceding discrete liquid has been completely drained therefrom through said container bore outlet means, and means to introduce at least one discrete liquid processing liquid to the container bore for concomitant containment therewithin with each of the discrete liquids. Outlet passage means can be operatively associated with the container bore outlet means for the flow and formation of an isolation liquid based stream of the discrete processed liquids thereinto from the container bore, and the supply of that stream to operatively associated analysis means for the successive analyses of the processed discrete liquids. Means can be provided to successively withdraw the processed discrete liquids from the container bore through the container bore inlet means for supply to operatively associated discrete liquid analysis means. Analysis means which operate through the transmission and detection of light energy can be operatively associated with the aligned container bore wall sections to successively analyze the processed discrete liquids in situ in the container bore. Immersion analysis means can be operatively associated with the container bore inlet means and successively immersible in the processed discrete liquids in the container bore to analyze the same in situ therein. Valve means can be operatively associated with the container bore outlet means to control the residence times of the discrete liquids and the processing liquids in the container bore.

OBJECTS OF THE INVENTION

It is, accordingly, an object of this invention to provide a new and improved, minimum carryover container.

It is another object of this invention to provide a container as above of particularly low cost.

It is another object of this invention to provide a container as above of particularly simple and reliable configuration and manner of operation.

It is another object of this invention to provide a container as above which has no moving parts.

It is another object of this invention to provide a container as above of virtually limitless re-usability.

It is another object of this invention to provide a container as above which totally eliminates the need for washing to accomplish the minimum carryover function thereof.

It is another object of this invention to provide a container as above of particularly wide versatility of application.

It is another object of this invention to provide a container as above which may be readily fabricated from readily available materials of proven dependability for the purposes thereof.

It is another object of this invention to provide a container as above which is particularly adapted to the successive containment of a series of discrete liquid samples with minimum sample liquid carryover therebetween.

It is another object of this invention to provide a container as above which is particularly adapted to the successive containment and processing in situ of a series of discrete sample liquids with minimum sample liquid carryover therebetween.

It is another object of this invention to provide a container as above which is particularly adapted to the successive analysis in situ of a series of discrete sample liquids with minimum sample liquid carryover therebetween.

It is another object of this invention to provide a container as above which is particularly adapted to the concomitant introduction thereinto of discrete sample liquids and sample processing liquids.

It is another object of this invention to provide a container as above which operates through use of an isolation liquid which is immiscible with said discrete sample liquids, and which is particularly adapted to the introduction of said isolation liquid thereinto independently of said discrete sample liquids.

It is another object of this invention to provide a container as above which is operable upon a large number of discrete sample liquids per unit time.

It is another object of this invention to provide a container as above which is particularly adapted to the formation of an isolation liquid based sample liquid stream comprising spaced segments of the discrete sample liquids with minimum carryover therebetween.

It is another object of this invention to provide a container as above with a very low rate of isolation liquid consumption.

It is another object of this invention to provide a container as above which is particularly adapted for use in automated successive sample analysis systems.

It is another object of this invention to provide a new and improved, automated successive sample liquid analysis system incorporating the container as above.

It is another object of this invention to provide an automated successive sample liquid analysis system as above which provides highly accurate sample liquid analysis results.

It is a further object of this invention to provide a sample liquid analysis system as above of simple and reliable configuration, low cost in terms of both system cost and system operational cost, and high speed in terms of the number of liquid samples that can be analyzed thereby per unit time.

DESCRIPTION OF THE DRAWINGS

The above and other objects and significant advantages of this invention are believed made clear by the following detailed description thereof taken in conjunction with the accompanying drawings wherein.

DETAILED DESCRIPTION OF THE INVENTION

Figure 1:
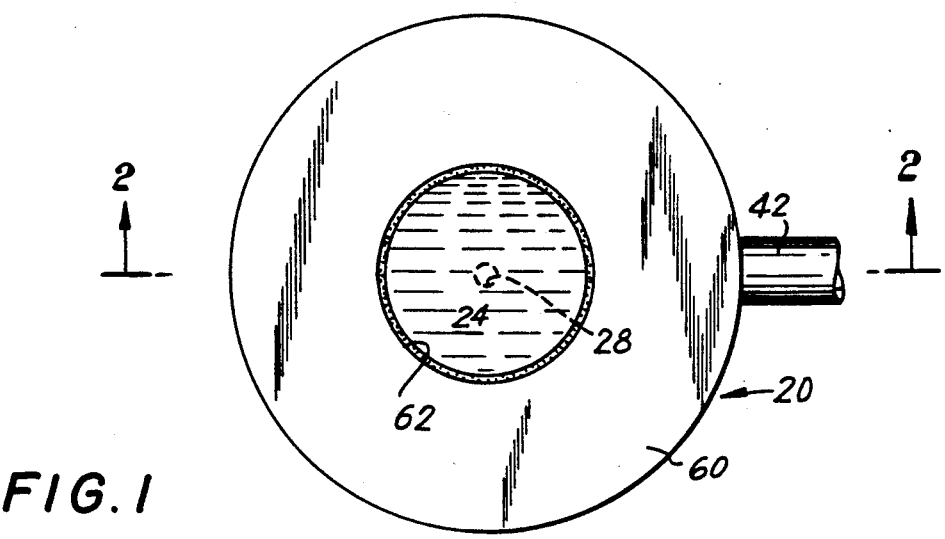
FIG. 1 is a top plan view of a first embodiment of a new and improved minimum carryover container configured and operable in accordance with the teachings of my invention.
Figure 2:
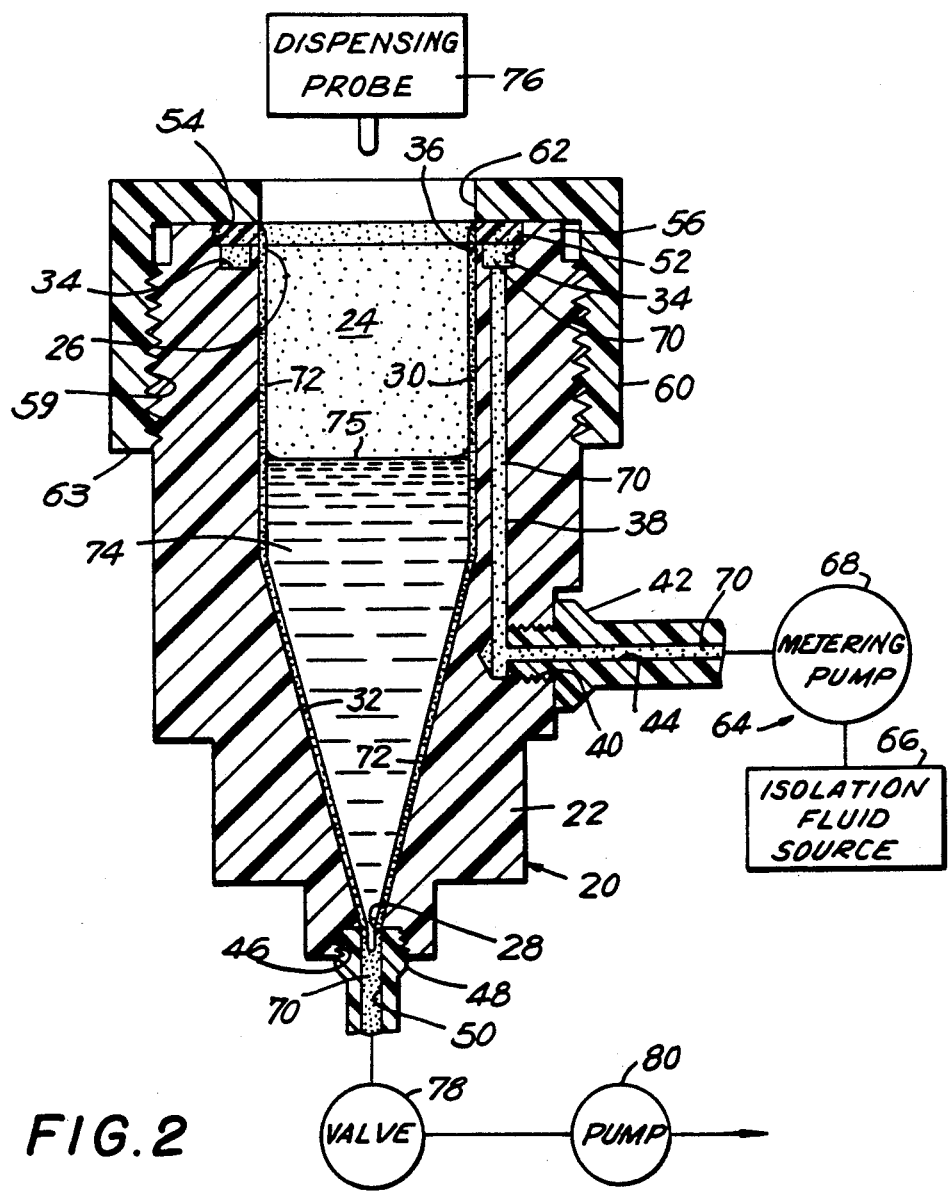
FIG. 2 is a cross-sectional view taken essentially along line 2—2 in FIG. 1.

Referring to FIGS. 1 and 2, a first embodiment of a minimum carryover container representatively configured and operable in accordance with the teachings of my invention is indicated generally at 20; and comprises a generally vertically oriented, generally cylindrical container body 22. A generally central internal space, taking for example the form of a funnel-like bore 24 is formed as shown in any appropriate manner to extend through container body 22 to provide a container inlet 26 and a container outlet 28. As utilized herein, the term "bore" is not intended as limitative of the configuration or manner of formation of the internal space in container body 22.

Figure 2A:
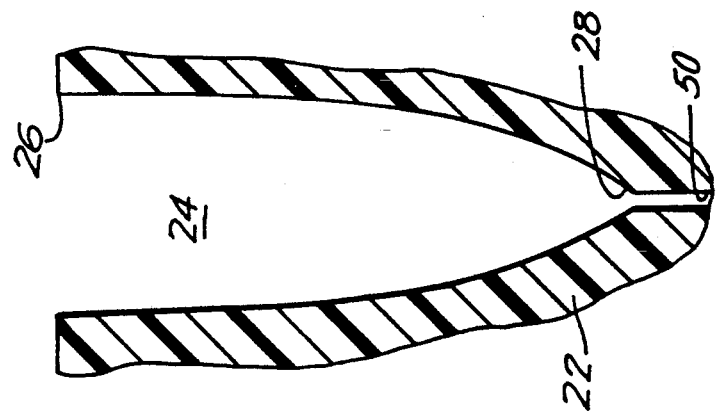
FIGS. 2A and 2B are simplified views in the nature of FIG. 2 which respectively illustrate alternative configurations for the bore of the container of FIGS. 1 and 2.
Figure 2B:
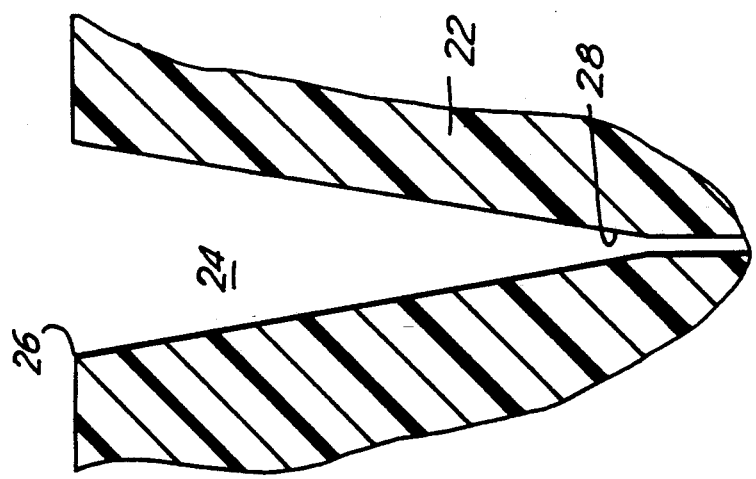

As representatively depicted in FIG. 2, bore 24 comprises an upper portion 30 of essentially cylindrical configuration to form container inlet 26; and an essentially frusto-conically configured lower bore portion 32 which is contiguous therewith and which tapers uniformly from the juncture thereof with upper bore portion 30 downwardly to form container outlet 28. Alternatively, container bore may take other and different configurations; for example essentially frusto-conical from container inlet 26 to container outlet 28 as depicted in FIG. 2A, or essentially parabolic from container inlet 26 to container outlet 28 as depicted in FIG. 2B. Of paramount importance in any event with regard to the configuration of container bore 24 is the fact that the same transition smoothly from container inlet 26 to container outlet 28 without any "hidden" spaces, or reverse taper or curvature, thus promoting smooth fluid flow through the bore from inlet 26 to outlet 28 for purposes described in detail hereinbelow.

With container bore 24 configured as described, it will be clear that inlet 26 and outlet 28 will be essentially circular; and although this configuration is most preferable for container outlet 28, it is not as important for container inlet 26 which may deviate therefrom in accordance with other and different configurations, not shown, for the container bore.

Container body 22 further includes an annular groove 34 formed as shown at the upper portion thereof to completely surround container inlet 26; and spaced therefrom as shown by an annular shoulder 36. A fluid passage 38 is formed in container body 22 to communicate the bottom of groove 34 with a tapped inlet port 40 formed in turn as shown to extend into the side wall of container body 22 below groove 34.

A threaded fluid inlet fitting 42, including fluid inlet passage 44, is secured as shown in tapped inlet port 40 to communicate fluid inlet passage 40 with the bottom of container body groove 34 through fluid passage 38. A tapped outlet port 46 is formed as shown at the bottom of container body 22 to completely surround container outlet 28; and a threaded fluid outlet fitting 48, including fluid outlet passage 50, is secured as shown in outlet port 46 to communicate container outlet 28 with fluid outlet passage 50 which is, of course, of the same size and configuration as the container outlet 28.

A porous annular washer 52 is disposed as shown in an annular mounting groove 54 provided therefor by shoulder 56 at the top of the container body 22 to completely surround the container inlet 26. This places the bottom surface of the porous washer 52 in communication with groove 34 throughout the entire respective annular extents thereof and, in conjunction with shoulder 36, effectively closes the top of groove 54.

The upper part of the container body 22 is externally threaded as indicated at 59; and an internally threaded, generally cylindrical container cap 60, which comprises a central bore 62 of essentially the same diameter as that of the cylindrical upper portion 30 of container bore 24, is screwed down atop the container body 22 as shown to align bore 62 and container bore portion 30, and to bear against the upper surface of porous washer 52 to retain the same in the depicted position thereof in mounting groove 54. In addition, container cap 60 functions to provide a shoulder 63 for mechanical support of the container 20 and to facilitate mounting thereof.

Isolation fluid supply means are schematically depicted at 64 in FIG. 2, and comprise a source 66 of an appropriate isolation fluid, and a metering pump 68 of precisely controllable pumping rate connecting source 66 to fluid inlet passage 44 in fitting 42 for the supply of isolation fluid to inlet passage 44 at precisely determinable flow rate(s). This results in the flow of the isolation fluid, as indicated at 70 in FIG. 2, through container body port 40 and passage 38 to annular groove 34 to soon completely fill the groove with isolation fluid and thereby surround the container inlet 28 with the isolation fluid. Under these circumstances, the isolation fluid 70 will come into contact with the underside of porous washer 52 which overlies groove 54, and will be soaked up in wick-like manner by the washer 52 to soon completely saturate the washer with the isolation fluid 70 throughout the entire 360° extent of the washer 52. Thus, as additional isolation fluid 70 is supplied to groove 34 by pump 68 for flow into contact with the underside of the isolation fluid-saturated washer 52, the isolation fluid already contained in the washer will ooze therefrom in uniform manner throughout the entire 360° extent of the washer t flow down the walls of container bore 24 from inlet 26 to outlet 28 under the influence of the force of gravity to completely and uniformly cover those walls with the isolation fluid. Thus, complete coating of the walls of container bore 24 with a constantly flowing stream or layer of of isolation fluid of uniform thickness, as indicated at 72 in FIG. 2, is assured, even in instances wherein the orientation of container body 22 deviates to a reasonable extent from the precisely vertical. This is to say that porous washer 52 uniformly distributes the isolation fluid 70 around the entire periphery of inlet 26, and uniformly introduces the same thereinto.

With steady state isolation fluid flow conditions established in accordance with the pumping rate of metering pump 68, and the viscosity and surface tension of isolation fluid 70, it will be clear to those skilled in this art that a stream or layer 72 of the isolation fluid 70 of optimal thickness can be readily established to constantly flow down and completely cover the walls of container bore 24 completely from inlet 26 to outlet 28; and to ultimately flow from the container bore 24 through outlet 28 into fluid outlet passage 50.

For use of the container 20 for the successive containment of, for example, discrete sample liquids of differing chemical characteristics without carryover, e.g. the contamination of a succeeding sample liquid by the residue of a preceding sample liquid, each of the container body 22, or at least the walls of container bore 24, porous washer 52, fluid outlet fitting 48, and container cap 60 are fabricated from materials which are substantially immune to "wetting" by the sample liquids; while the isolation fluid 70 is made up from a liquid which will very readily and selectively "wet" the those materials to the substantial exclusion of the sample liquids, and which is immiscible with those liquids. This phenomenon of selective "wettability" is described in some detail in U.S. Pat. No. 3,479,141.

With the components of container 20, and the isolation liquid 70, respectively constituted and physically characterized as specified directly hereinabove vis-a-vis the sample liquids, it will be clear that nay of the sample liquids, one of which is representatively depicted at 74 in FIG. 2, resident in container bore 24 following the introduction and flow as described of the isolation liquid stream 72 will be effectively prevented by that stream from contact with, and thus adherence to, the walls of container bore 24. Instead, those relevant molecules of the sample liquid 74 which reside at the extremely low friction interface of the sample liquid with the constantly flowing isolation liquid stream 72 will be maintained spaced by the latter from the walls of the container bore 24 for ultimate drainage along with the bulk of the sample liquid 74 from the container bore 24 through outlet 28 into outlet passage 50. This is to say that the sample liquid 74 will in essence remain "whole" and isolated from the walls of container bore 24 by the isolation liquid stream 72, and will simply flow down and out of container bore 24 as a unit without contact with or adherence to the container bore walls. Of course, the naturally low friction between liquids will very substantially inhibit, if not virtually totally prevent, adherence of the sample liquid 74 to the extremely "slippery" or virtually zero drag surface of the immiscible isolation liquid stream 72 which is, in any event, also flowing downwardly under the force of gravity, albeit in most instances at a lower velocity, for ultimate drainage therefrom through container bore outlet 28 into outlet passage 50. Thus, it will be clear to those skilled in this art that virtually no residue of the sample liquid 74 will remain in container bore 24 to contaminate succeeding sample liquids as may be introduced thereinto. Normally, a very thin layer of the isolation liquid 70, as indicated at 75 in FIG. 2, will form atop the sample liquid 74; but this is of no consequence regarding carryover in that the isolation liquid layer 75 will, of course, simply drain with the sample liquid from the container bore 24.

Introduction of successive sample liquids to the container bore 24 on an appropriately timed basis to insure that, in each instance, a preceding sample liquid has been completely drained therefrom prior to the introduction of a succeeding sample liquid thereinto, may be accomplished in any convenient and practical manner, for example, by standard sample liquid dispensing probe means as indicated schematically at 76 in FIG. 2.

A residence time for the sample liquid 74 in container bore 24 of longer duration than that which would be required for the same to to drain completely therefrom through bore outlet 28 under the influence of the force of gravity, may be readily provided for by the utilization of appropriate valve means as schematically indicated at 78 in FIG. 2 which are operable to close container bore outlet passage 50. With valve means 78 closed to this effect, isolation liquid stream 72 will nonetheless continue to flow down the walls of container bore 24 under the influence of the force of gravity; with the isolation liquid 70 for the most part simply accumulating or "pooling up" at the bottom of the container bore 24 until such time as the valve means 78 are opened, or reopened as the case may be, and the accumulated isolation liquid 70, and the sample liquid 74 permitted to drain from the container bore 24 through outlet 28. In such instances, and wherein sample liquid drainage time from the container bore might be a factor, appropriate evacuation pump means as schematically indicated at 80 in FIG. 2 could be operatively disposed as shown downstream of valve means 78 to be effective upon opening thereof to more rapidly evacuate the sample liquid 74 and, of course, the accumulated isolation liquid 70, from the container bore 24.

For use of the container 20 wherein the successively contained sample liquids are aqueous liquids, container body 22, or at least the walls of container bore 24, porous washer 52, fluid outlet fitting 48 and container cap 60 are preferably fabricated from any one of a wide range of readily available, generally inert fluorinated hydrocarbon solid materials of low surface energy and proven stability; while isolation liquid 70 is preferably made up from any one of a wide range of fluorinated or perfluorinated hydrocarbon liquids which are also generally inert and stable, and which exhibit low surface tension and appropriate viscosity. Non-limitative examples of these solid and liquid hydrocarbon materials are polytetrafluoroethylene and perfluorodecalin, respectively.

Figure 3:
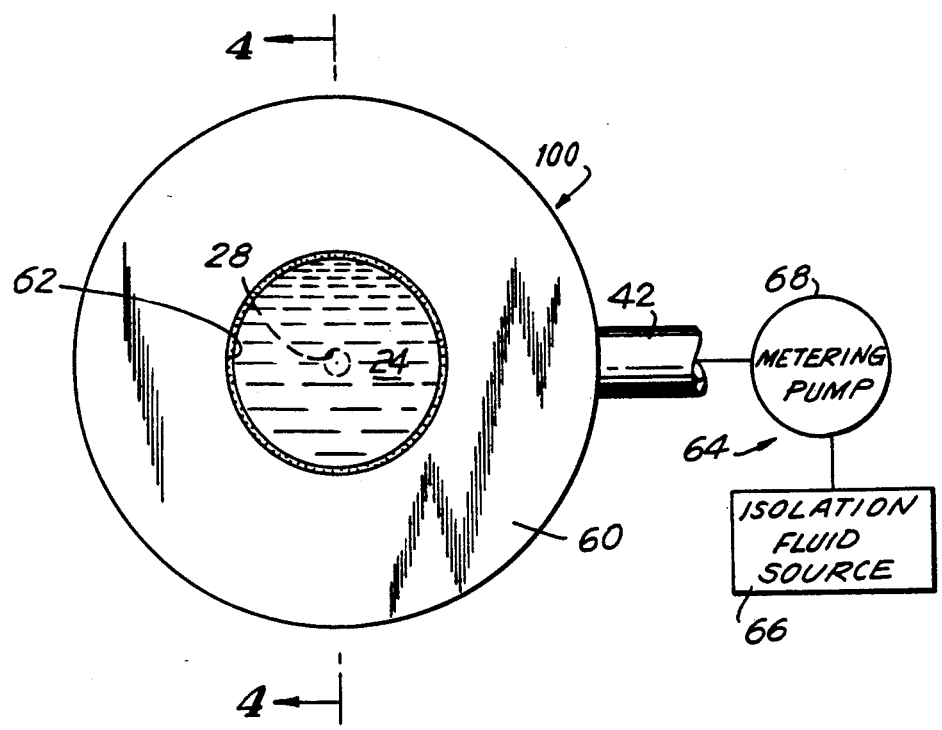
FIG. 3 is a top plan view of a second embodiment of a minimum carryover container configured and operable in accordance with the teachings of my invention.
Figure 4:
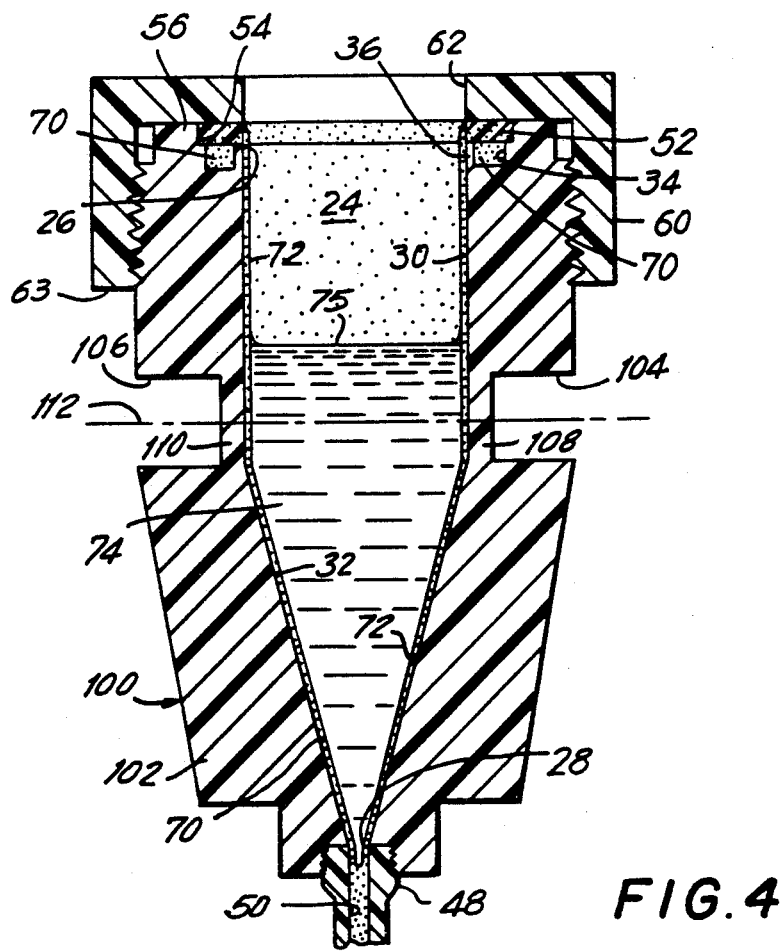
FIG. 4 is a cross-sectional view taken essentially along line 4—4 in FIG. 3.

A second embodiment of a minimum carryover container representatively configured and operable in accordance with the teachings of my invention is indicated generally at 100 in FIGS. 3 and 4. Container 100 comprises a generally cylindrical container body 102 which differs somewhat from container body 22 of FIGS. 1 and 2 as described in detail hereinbelow. In all other structural aspects of significance, container 100 is virtually the same as container 20 of FIGS. 1 and 2; and like reference numerals are accordingly used to identify like container structure throughout FIGS. 1, 2, 3 and 4. Container body 102 differs from container body 22 in comprising co-axial, generally aligned bores 104 and 106 formed as shown in opposite side walls thereof to extend thereinto toward container bore portion 30 and terminate just short of the latter to result in aligned, generally annular container bore wall sections 108 and 110 of substantially reduced thickness disposed as shown to opposite sides of container bore portion 30. This in essence provides aligned viewing windows in the container body 102 for the viewing from without the container 100 of sample liquids 74 disposed in the container bore 24.

More specifically, it will be readily understood by those skilled in this art that: with bores 104 and 106 formed to extend sufficiently into container body 102 to result in container bore wall sections 108 and 110 of the minimum thickness compatible with the operational structural integrity of container body 102; with container body 102 being fabricated from, for example, an appropriate fluorinated hydrocarbon solid material which will, under those circumstances, be substantially transmittive of light energy; with the thickness of isolation liquid stream 72 being determined by control of the pumping rate of metering pump 68 to result in an isolation liquid stream of the minimum thickness compatible with the container bore isolation function thereof vis-a-vis the sample liquids; and with the isolation liquid 70 being made up from, for example, an appropriate fluorinated or perfluorinated hydrocarbon liquid of substantially the same refractive index as that of the container body material, and which will, under those circumstances, also be substantially transmittive of light energy as is characteristic of those materials; it becomes possible to transmit light energy from without the container 100 through, for example, container bore wall section 108, isolation liquid stream 72, the liquid 74 which is, of course, also assumed to be somewhat transmittive of light energy, isolation liquid stream 72, and container bore wall section 110, respectively; and to meaningfully detect the thusly transmitted light energy in terms of accurately quantifying the extent of the attenustion thereof which is caused by the liquid 74. If necessitated by optical consideration, the internal surfaces of container bore wall sections 108 and 110 may be somewhat flattened, not shown, to maximize collimation of light energy as transmitted therethrough.

Advantageously, the side wall bores 104 and 106 are formed in container body 102 at a location which insures that the coincident axis of those bores passes through the portion 30 of container bore 24 of maximum diameter. This insures that the sight path provided as described hereinabove through liquid 74 along axis 112 is of maximum length vis-a-vis the respective thicknesses of container wall sections 108 and 110, and the relevant thicknesses of the isolation liquid stream 72; thus in turn insuring that the ratio of light energy attenuation by walls 108 and 110 and the isolation liquid stream 72, to light energy attenuation by liquid 74, is minimized.

Figure 5:
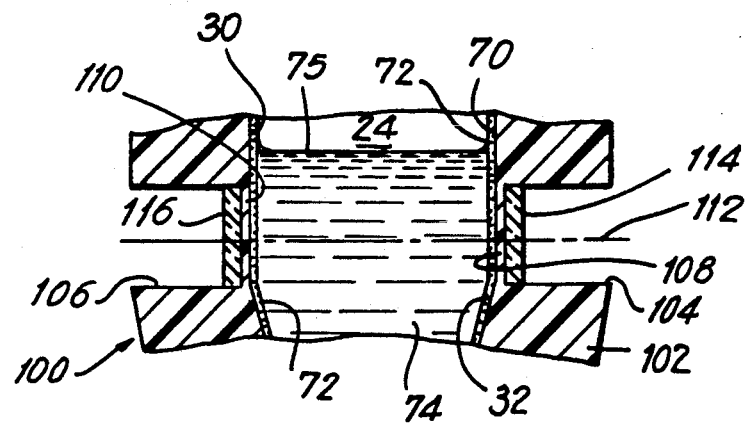
FIG. 5 is a cross-sectional view in the nature of FIG. 4 taken through a relevant portion of a modification of the container of FIGS. 3 and 4.
Figure 6:
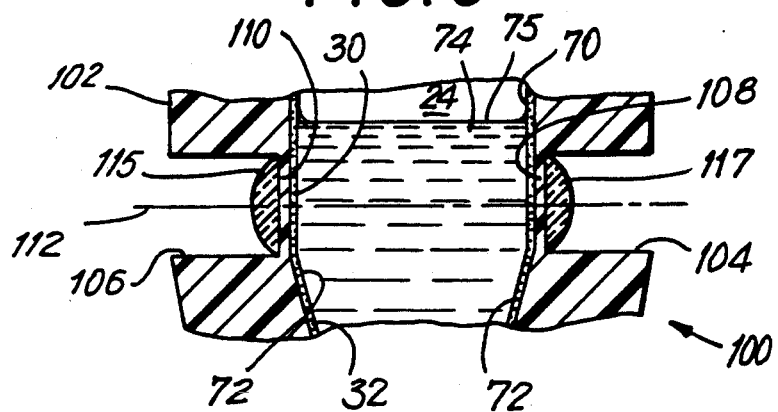
FIG. 6 is a cross-sectional view in the nature of FIG. 4 taken through a relevant portion of another modification of the container of FIGS. 3 and 4.
Figure 7:
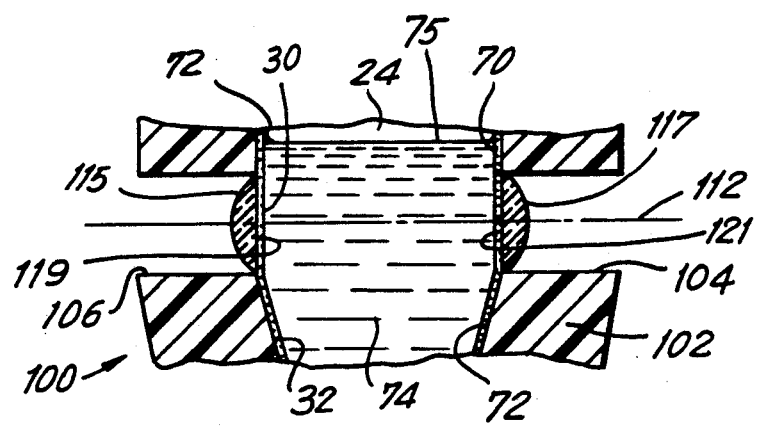
FIG. 7 is a cross-sectional view in the nature of FIG. 4 taken through a relevant portion of a further modification of the container of FIGS. 3 and 4.

A modification of the container body 102 is depicted in FIG. 5, and comprises the disposition as shown of appropriately configured transparent window members 114 and 116 at the respective inner extermities of bores 104 and 106 in surface contact with the external surfaces of container bore wall sections 108 and 110. With, for example, window members 114 and 116 being made from a high strength glass material, it will be clear that the wall sections 108 and 110 can be even further reduced in thickness as shown to significant light transmission advantage without adverse effect on the operational structural integrity of the container body 102. FIG. 6 depicts this modification wherein the window members are configured as lenses 115 and 117; and can thus function to optically enhance light energy transmission along the sight path of interest in addition to making possible the further reduction in thickness of container bore wall sections 108 and 110. FIG. 7 depicts the further modification of the container body 102 wherein the lenses 115 and 117 actually form the container body wall sections of interest to thus maximize light energy transmission under the described circumstances. In this instance, the respective inner surfaces of the lenses 115 and 117 which here actually form parts of the container bore walls would, of course, be coated or otherwise treated as indicated at 119 and 121 in FIG. 7 to exhibit the same characteristics as described hereinabove vis-a-vis the isolation liquid 70 and the sample liquid 74 as the material from which the container body 102, or at least the walls thereof, is made.

Figure 8:
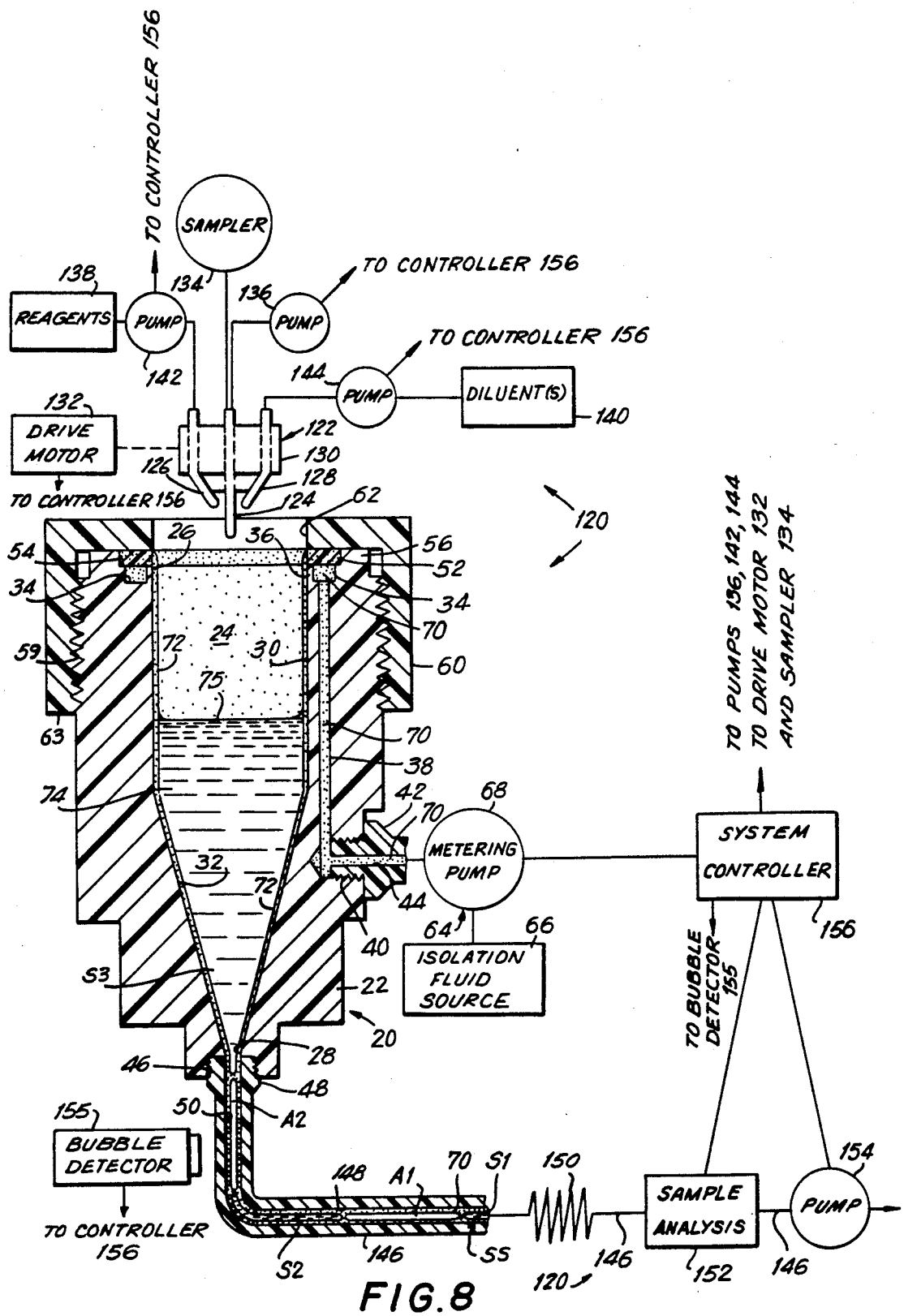
FIG. 8 is an essentially diagrammatic view of a first embodiment of a new and improved sample analysis system configured and operable in accordance with the teachings of my invention, and includes the cross-sectional view of the container of FIGS. 1 and 2.

A first embodiment of an automated sample liquid analysis system representatively configured and operable in accordance with the teachings of my invention is indicated generally at 120 in FIG. 8. Operation of automated sample liquid analysis systems of this nature, which are generally effective to automatically treat as required, form into a continuously flowing stream, and analyze in trun each of a series of discrete sample liquids with regard to the respective concentration(s) of one or more analytes as contained in the sample liquids, are disclosed in detail in U.S. Pat. Nos. 3,479,141, and 4,253,846, currently pending application for U.S. Pat. Ser. No. 441,181; and U.S. Pat. No. 3,241,432 as here also incorporated by reference.

With specific regard to system 120, the same comprises the minimum carryover container 20 of FIGS. 1 and 2. Ganged dispensing probe means are indicated generally at 122, and comprising dispensing probes 124, 126 and 128 supported as shown from a common probe support body 130. Probe drive motor means are schematically indicated at 132, and are operable to mechanically drive the probe means 122 to position the same as desired with regard to container 20. Probe 124 is operable to successively dispense, at predetermined like time intervals, predetermined like quantities of discrete sample liquids, as aspirated thereinto from sampler means as schematically indicated at 134 by pump means as schematically indicated at 136, in turn into container bore 24; while probes 126 and 128 are operable to concomitantly, or after predetermined time intervals, dispense like predetermined quantities of sample liquid reagents and diluents, provided thereto from reagent and diluent liquid sources as schematically indicated at 138 and 140 by pump means as schematically indicated at 142 and 144, into container bore bore 24 for mixing therewithin with the sample liquid of interest in each instance.

Dispensing as described of the respective sample, reagent and diluent liquid quantities is preferably at relatively high velocity; and dispensing probes 126 and 128 are preferably angled as shown relative to dispensing probe 124 and to container bore inlet 26 to promote ballistic mixing of the respective sample, reagent and diluent liquid quantities upon the introduction thereof into container bore 24. Of course, nothing is ever dispensed into container bore 24 with sufficient energy to destroy or in any significant way impair the integrity of isolation liquid stream 72. As an alternative to the above, the dispensing probe means 122 may take the form of those disclosed in U.S. Pat. No. 4,121,466 which offer the additional advantage of utilizing an appropriate isolation liquid to minimize sample liquid carryover attendant the supply thereof.

For use of the container 20 in the analysis system 120, the minimum diameter of the container inlet 26 is determined to be that which will readily enable the dispensing of liquids thereinto by probe means 122; it being noted in this regard that the operative ends of each of the probes 124, 126 and 128, rather than just the former as shown in FIG. 8, may be positioned by probe drive motor means 132 to extend below the rim of contain cap 60 for the dispensing of liquids into the container bore 24. The maximum diameter of the container bore outlet 28, and thus of the outlet passage 50 in outlet fitting 48 is determined to be that which will insure that the isolation liquid 70, and an inter sample liquid bubble or segment of air which is formed as described in detail hereinbelow in outlet passage 50, completely occlude the container bore outlet 28 as the same respectively drain and are forced from the container bore 24. A flexible outlet conduit is indicated at 146, and is connected to outlet fitting 48 in any appropriate manner, not shown. The outlet conduit is made from the same fluorinated hydrocarbon material as discussed hereinabove with regard to container body 22, and the outlet conduit 146 includes an outlet passage 148 of the same diameter as and contiguous with outlet passage 50 in fitting 48.

Additional sample liquid processing means, for example a mixing coil as depicted at 150 and taking the form of that disclosed in U.S. Pat. No. 4,422,773 of M. M. Cassaday, et al, are formed as shown by the outlet conduit 146 downstream of the container body outlet 28. Sample analysis means are depicted schematically at 152 and may, for example, take the form of appropriate colorimeter means which are operable in well known manner to detect the change in color of each of the discrete sample liquids resulting form the mixture and reaction thereof with the reagent(s) from source 138, and to provide an output signal indicative thereof, and thus of the concentration(s) of the sample liquid analyte(s) in each instance. The analysis means 152 are disposed as shown in conduit 146 downstream of mixing coil 150. A sample liquid stream pump is schematically indicated at 154 and is operatively disposed as shown in outlet conduit 146 downstream of the sample analysis means 152. Pump 154 operates to insure the flow of the sample liquid stream from container bore 24 in outlet conduit 146 through the sample analysis means 152 at substantially constant, predeterminable flow rate, commensurate, of course, with the rate of operation of the dispensing probe means 122. Air bubble detector means are indicated schematically at 155, and are operatively associated as shown with the outlet conduit 146 to sense the leading edge of each air bubble in turn as the same enter that conduit, thus insuring that the sample liquid has completely drained therefrom in each instance, for purposes described in detail hereinbelow.

A system controller is indicated schematically at 156, and is operatively connected as shown to each of pumps 154, 126, 142, 144 and 66, sample analysis means 152, bubble detector means 155 and dispensing probe drive motor means 132, and is operable to control and synchronize the operation of sample analysis 120 with regard to the formation of the sample liquid stream and the sequential analyses of the respective discrete sariple liquids as contained therein.

With the sample analysis system 120 configured as described for the analysis in turn of successive aqueous sample liquids, it will be clear that as each diluted and reacted sample liquid quantity 74 flows from container bore 24 through outlet 28 and passage 50 in outlet fitting 48 into and through outlet conduit passage 148, the same will be effectively encapsulated by the concemitantly flowing isolation liquid stream 72 to form a discrete sample liquid segment which is prevented as described by the isolation liquid 70 from contact with the respective walls of outlet passages 50 and 148. This, of course, prevents contamination of those walls by that sample liquid quantity. One such sample liquid quantity taking the form of a sample liquid segment is indicated at S1 in conduit passage 148 in FIG. 8. Of course, upon the completion of the evacuation of this diluted and reacted sample liquid quantity which forms segment S1 from container bore 24, ambient air will fill the container bore 24 and begin to enter outlet passage 50 to form the beginning of an occluding air bubble or segment, the leading edge or interface of which becomes surrounded as shown by the concomitantly draining isolation liquid 70 to thus form a carryover-preventing seal at the downstream side of the preceding sample liquid segment. One such air segment or bubble is indicated at A1 in FIG. 8. As the leading edge of this air segment flows past the bubble detector means 155 to indicate that the preceding sample liquid quantity has been completely drained from the container bore 24, the same is detected by the bubble detector means 155 which operates in response thereto through controller means 156 to key the dispensing probe means 122 to introduce the succeeding sample, reagent and diluent liquid quantities into container bore 24. These liquid quantities will flow downwardly in container bore 24 under the influence of the force of gravity displacing the ambient air therefrom until a bore diameter is reached whereat ambient air can no longer be displaced by these incoming liquids, and an air bubble is entrapped therebelow in the bore. This bore diameter or zone of bore occlusion by the incoming liquids will be a function of surface tension and, to some degree, the flow velocity in question. Accordingly, the thusly entrapped air quantity will be forced to precede the succeeding diluted and reacted sample liquid quantity in flowing from container bore 24 into outlet passages 50 and 148 for encapsulation by the constantly flowing isolation liquid stream 72 to complete the formation of the air segment as indicated at A1 in FIG. 8.

The succeeding diluted and reacted sample liquid quantity the flows from the container bore 24 through outlet 28 into outlet passages 50 and 148 for encapsulation as described by the isolation liquid 70 to form the succeeding sample liquid segment as indicated at S2 in FIG. 8; closely followed as shown by the succeeding air segment A2. This cycle is, of course, repeated as described until all diluted and reacted sample liquid quantities of interest have been dispensed in turn into container bore 24 by dispensing probe means 122, and flowed therefrom in turn into outlet conduit passage 148 to form the depicted, isolation liquid based, air segmented sample liquid stream as indicted generally at SS in FIG. 2.

The thusly generated stream SS is then flowed at substantially constant flow rate by pump 154 through mixing coil 150 for additional mixing as may be required of the respective sample, diluent and reagent quantities as make up each of the sample liquid stream segments, without adverse on the hydraulic integrity of those segments, and therefrom to colorimeter 152 for successive analysis in trun of the respective sample liquid segments S1, S2, S3, etcetera. The automated analysis of isolation liquid based sample liquid streams of the nature of stream SS, and the significant advantages thereof regarding the minimization of sample liquid carryover with attendant optimization of the accuracy of the analysis results, are described in detail in U.S. Pat. Nos. 3,479,141 and 4,253,846, and in assignee's copending application for U.S. Pat. No. Ser. No. 441,881.

Of particularly significant additional advantage with regard to automated sample analysis system 120 is that the same functions, through use as described of the simple container 20 as a system "front end," to effectively generate the isolation liquid based sample liquid stream at very substantially lower cost, and through the use of system components of far lesser complexity, and with a far greater degree of reliability, than the analogous systems of the prior art as discussed in some detail hereinabove. In fact this reduction in cost with regard to the generation of isolation liquid based sample liquid stream SS has been calculated to be in the range of a full ten fold reduction when compared to the cost of the "front end" mechanism required for isolation liquid based sample liquid stream generation in the automated sample analysis system of U.S. Pat. No. 4,253,856. In addition, the introduction of the isolation liquid to the system 120 as described in manner independent of the operation of dispensing probe means 122 —as clearly opposed to the use of the dispensing probe means for that purpose in the relevant prior art as discussed hereinabove —leaves the probe means totally free in accordance with the teachings of my invention for sample, diluent and reagent dispensing to thus provide for significantly increased overall speed of operation of the analysis system 120, and in no way intefere with the essentially precise sample, diluent and reagent liquid quantities metering function of the probe means. Speed of operation of the analysis system 120 is further increased by the fact that, with no moving parts, the speed of operation as described of container 20, i.e. the time required for the respective sample, reagent and diluent liquid quantities for each discrete sample to be dispensed into and drain from the container bore 24, is limited primarily be drainage time which is generally longer. Thus, and with complete drainage times for the container bore of as little as one second having proven practically achievable, it will be clear to those skilled in this art that particularly high speed of operation can be achieved by container 20 with regard to the effective mixing of the respective sample, diluent and reagent liquid quantities of interest in each instance, and the effective generation of the isolation liquid based sample liquid stream SS therefrom. This is, of course, of significant financial advantage with regard to utilization of the automated sample analysis system 120.

For clarity of illustration and description with regard to the analysis system 120 of FIG. 8, the respective thicknesses of the isolation liquid stream 22 in container bore 24, and of the isolation liquid layers which completely encapsulate the respective successive sample liquid and air segments in outlet passages 50 and 148 are, of course, exaggerated; it being clear to those skilled in this art that, in actual practice, the same would be thinner.

Figure 9:
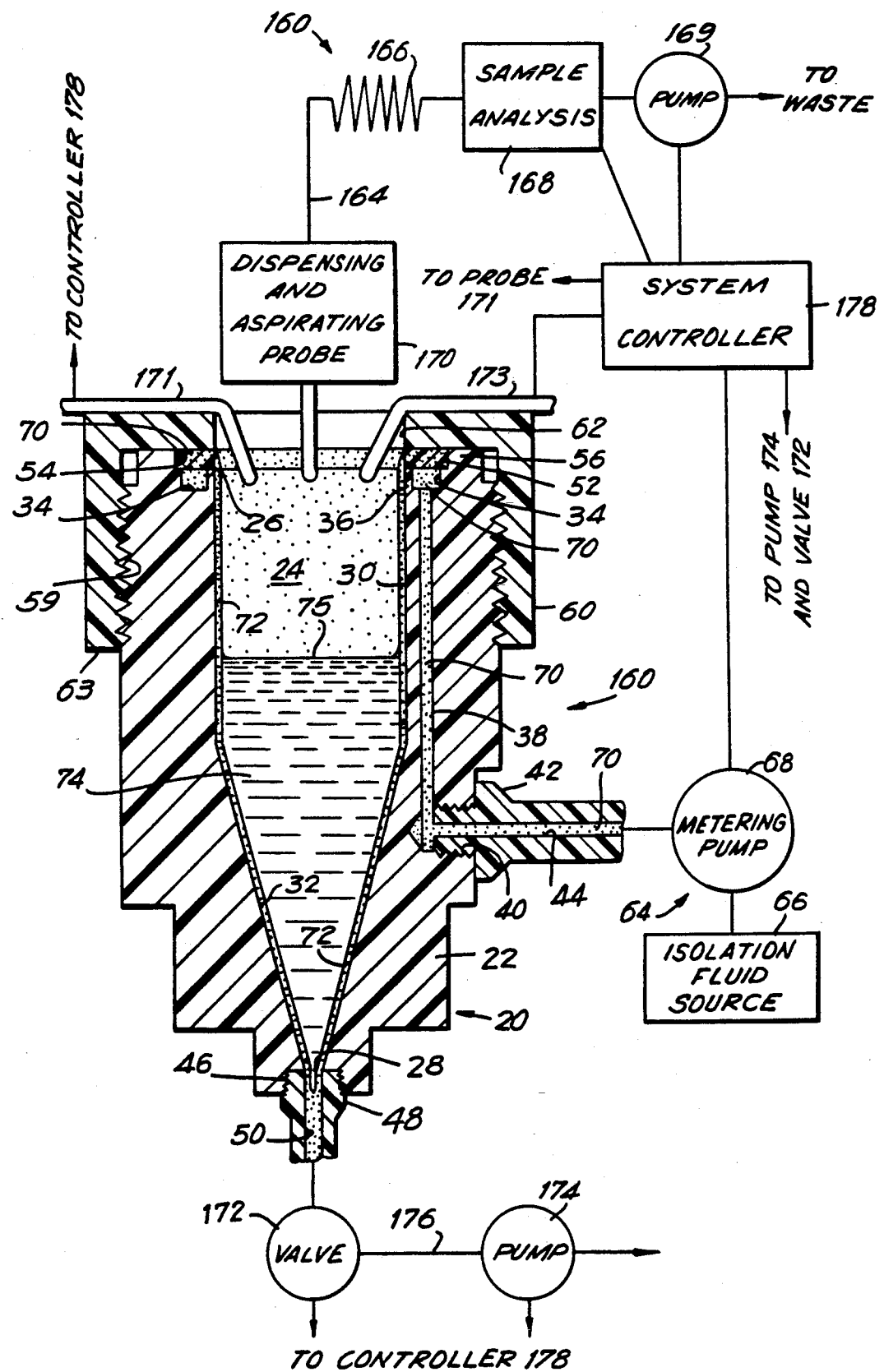
FIG. 9 is an essentially diagrammatic view of a second embodiment of a sample analysis system configured and operable in accordance with the teachings of my invention, and includes a cross-sectional view of the container of FIGS. 1 and 2.

A second embodiment of an automated sample analysis system representatively configured and operable in accordance with the teachings of my invention is indicated generally at 160 in FIG. 9; and again comprises the minimum carryover container 20 of FIGS. 1 and 2. In this embodiment, the container functions primarily as a sample liquid dilution and reaction, or pre-dilution and pre-reaction, vessel; with the respective sample, diluent and reagent quantities being introduced thereinto for sample liquid dilution and reaction, and predetermined quantities of the thusly diluted and reacted sample liquid quantities a again indicated at 74 then being aspirated therefrom for supply along a supply conduit as schematically indicated at 164 through additional sample liquid processing means, again for example a mixing coil as schematically indicated at 166, to automated sample liquid analysis means 168 again taking the form, for example, of a colorimeter. Pump means as schematically indicate at 169 are provided as shown downstream of colorimeter 168 in supply conduit 164 to insure constant flow rate through the colorimeter.

Dispensing and aspirating probe means are indicated schematically at 170, and are operable to dispense successive sample liquid quantities in turn into bore 24 of container 20 from a non-illustrated source thereof, and to successively diluted and reacted sample liquid quantities in trun from bore 24 for supply along conduit 164 to the sample analysis means 168. To this effect, probe means 170 may, for example, take the form of those disclosed in U.S. Pat. No. 4,121,466.

Diluent and reagent dispensing probes are indicated schematically at 171 and 173, and are respectively operable to successively dispense diluent and reagent quantities into container bore 24 from non-illustrated sources thereof. Since probe means 171 and 173 are not required to move attendant the described functions thereof, the same may readily be supported from the container cap 60 as indicated, thus simplifying the analysis system 160.

Further included in the sample analysis system 160 are valve means as schematically indicated at 172 and pump means as schematically indicated at 174, respectively disposed as shown along a container body outlet conduit as schematically indicated at 176. Valve means 172 and pump means 174 are respectively operable to control the residence time of the sample, diluent and reagent liquids in container bore 24, and to speed the drainage of the same from bore 24 through outlet 28 along outlet conduit 176 as may be required.

A system controller is indicated schematically at 178 in FIG. 9, and is operatively connected as indicated to each of pumps 68, 169 and 174, valve 172, dispensing and aspirating probe means 170, and dispensing probe means 171 and 173 to control and synchronize the respective operations thereof.

With sample liquid analysis system 160 of FIG. 9 configured as described for the automated successive analyses of aqueous sample liquids, it will be clear that with the isolation liquid stream 72 flowing as described to completely cover the walls of container bore 24, and valve means 172 closed, the respective predetermined quantities of the sample, reagent and diluent liquids for the first sample liquid of interest are dispensed by dispensing probe means 170, 173 and 171 concomitantly into container bore 24 for sample liquid dilution and reaction. Once this has occurred, and the reaction complete, probe means 170 are operated to aspirate a predetermined quantity of the diluted and reacted sample liquid from container 20 for supply as indicate to supply conduit conduit 164. As this is completed, valve means 172 are opened and pump means 174 activated as required for the drainage of the the remaining liquid quantity for the first sample liquid of interest from container bore 24 to waste, or to a separate analytical system, not illustrated, along outlet conduit 176. As drainage is completed, valve means 172 are again closed, and the respective predetermined sample, reagent and diluent quantities for the succeeding sample liquid of interest are respectively dispensed by probe means 170, 173 and 171 into container bore 24 for repetition of the cycle as described.

This process is, of course, repeated in turn for each of the sample liquids of interest; thus resulting in the formation of a sample liquid stream, not shown, containing successive discrete segments of each of the sample liquids of interest —which may be separated by any appropriate separation fluid(s) in manner(s) well known to those skilled in this art—for supply along supply conduit 164 by pump means 169 to sample analysis means 168 for successive sample liquid analysis. Of particular advantage with regard to analysis system 160 of FIG. 9 are again low cost, high speed of operation, high degree of reliability and, of course, minimization of sample liquid carryover, all in this instance as related to sample liquid dilution and reaction.

A third embodiment of an automated sample liquid analysis system representatively configured and operable in accordance with the teachings of my invention is indicated generally at 180 in FIG. 10, and again comprises the minimum carryover container 20 of FIGS. 1 and 2. In this embodiment, container 20 effectively functions as the situs for both sample liquid dilution and reaction, and sample liquid analysis, thus even further simplifying the sample analysis process by rendering unnecessary the formation and transport of the sample liquid stream to the sample analysis means.

Figure 10:
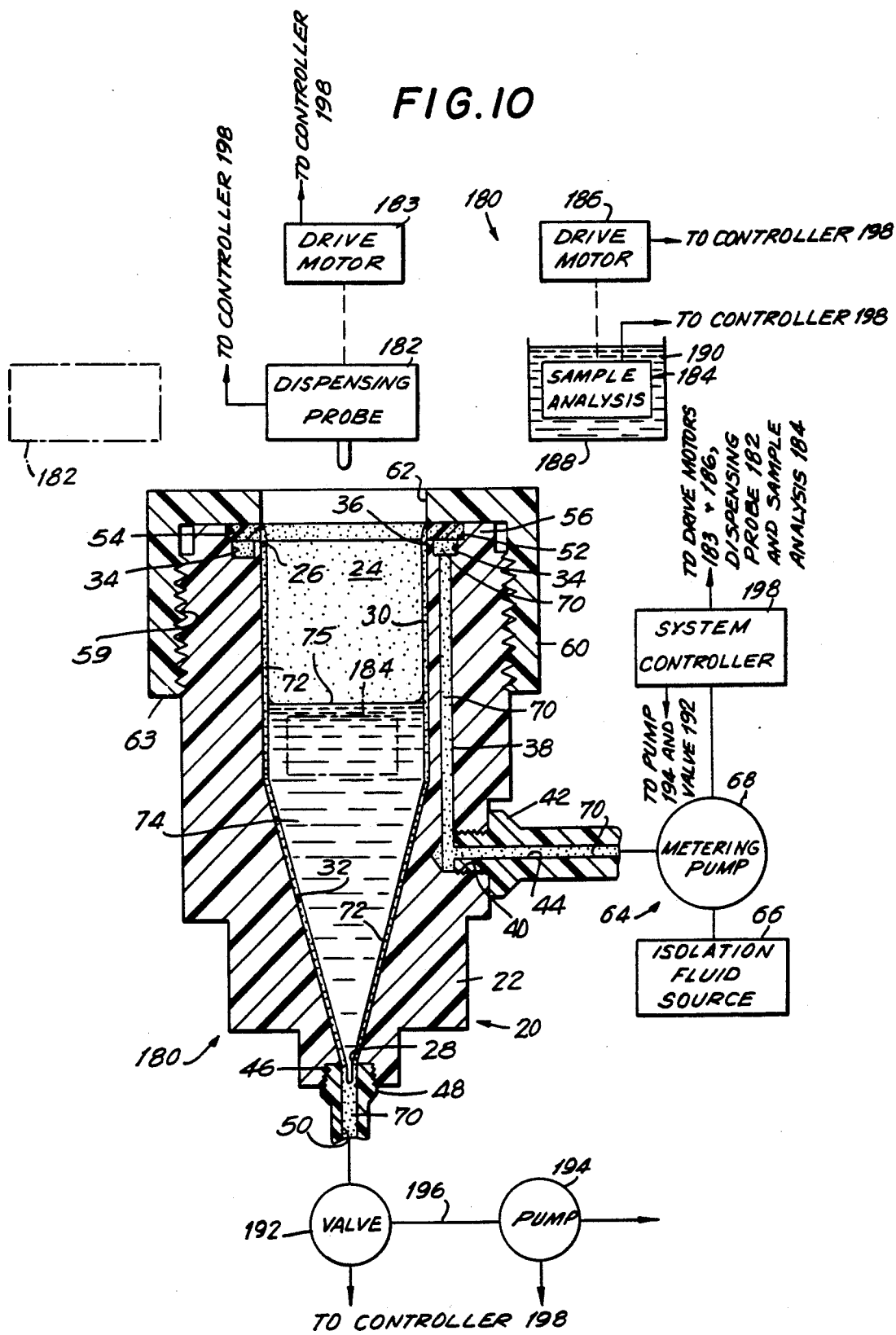
FIG. 10 is an essentially diagrammatic view of a third embodiment of a sample analysis system configured and operable in accordance with the teachings of my invention, and includes a cross-sectional view of the container of FIGS. 1 and 2

Dispensing probe means operable to dispense predetermined sample, diluent and reagent liquid quantities from respective sources thereof, not shown, into container bore 24, are indicated schematically at 182 in FIG. 10; and dispensing probe means drive motor means as schematically indicated at 183 are operable to move the same between a first probe means position as shown wherein the probe means are operable to dispense liquids into container bore 24, and a second probe means position as depicted in phantom in FIG. 10 wherein the probe means 182 are not so operable and do not impede access to container bore 24. Probe means 182 may, for example, take the form of the ganged probe means 122 of FIG. 8 to include all of the pump, liquid source and conduit means as depicted therein. Alternatively, dispensing probe means 182 may take the form of the liquid dispenser with improved probe as disclosed in U.S. Pat. No. 4,121,466.

Sample liquid analysis means are schematically depicted at 184 in FIG. 10, and include drive motor means 186 mechanically connected thereto as indicated and operable to drive the same between a first analysis means position wherein the analysis means are without the container bore 24 as shown and do not impede access thereto by the probe means 182, and a second analysis means position as depicted in phantom in FIG. 10 wherein the analysis means 184 are disposed in the container bore 24 and immersed in the sample liquid 74 contained therein. To this effect, sample analysis means 184 are constituted by immersion analysis means taking, for example, the form of an immersion colorimeter or immersion electrodes. A wash liquid receptacle is indicated schematically at 188 in FIG. 10, and includes a quantity of an appropriate sample liquid wash liquid 190, for example water for aqueous sample liquids, which may be flowing through the receptacle from an appropriate source, and from the latter to waste. With analysis means 184 disposed in the first position thereof, the same are submerged as shown in the that wash liquid to remove sample liquid residue therefrom and minimize sample carryover as might otherwise result from contamination of the analysis means 184.

Valve means are schematically indicated at 192, and pump means are schematically indicated at 194 in FIG. 10; and are respectively disposed as shown in container body outlet conduit as schematically indicated at 196 for the purposes described hereinabove with regard to FIGS. 2 and 9.

A system controller is indicated schematically at 198 in FIG. 10, and is operatively connected as indicated to each of drive motor means 184 and 186, dispensing probe means 182, pumps 68 and 194, and valve 192 to control and synchronize the respective operations thereof.

With sample liquid analysis system 180 of FIG. 10 configured as described for the automated successive analyses of aqueous sample liquids in situ in container bore 24, it will be clear that with the isolation liquid stream formed and flowing as described to completely cover the walls of container bore 24 from bore inlet 26 to bore outlet 28, with valve means 192 closed, with dispensing probe means 182 disposed in the first position thereof for the dispensing of liquids into container bore 24, and with sample analysis means 184 disposed in the first position thereof in wash liquid receptacle 188 without the container bore, respectively, probe means 182 may be operated to dispense the respective predetermined quantities of the sample, diluent and reagent liquids for the first sample liquid of interest into container bore 24 for sample liquid dilution and reaction. Once this has been completed, probe means 182 are moved by drive motor means 183 to the second position thereof to provide access to the container bore 24 for the sample analysis means 184; and the analysis means 184 are moved by the drive motor means 186 into the second position thereof for immersion as shown in the now appropriately diluted and reacted sample liquid 74 to analyze the same in situ in container bore 24.

Once sample liquid analysis has been completed, the analysis means 184 are returned to the first position thereof within wash liquid receptacle 184 to remove the residue of the first sample liquid therefrom; and valve means 192 opened and pump means 194 activated to enable the drainage of the accumulated isolation liquid 70 and the diluted and reacted first sample liquid completely from the container bore 24, and the flow thereof to waste, or to other analysis means, not shown, along outlet conduit 196. Once the analysis means 184 are clear of the container bore 24, probe means 182 are returned to the first position thereof by drive motor means 183 and, upon complete drainage of the diluted and reacted first sample liquid as described and re-closing of valve means 192, are operable to dispense the respective predetermined quantities of the sample, diluent and reagent liquids for the second sample liquid of interest into container bore 24 for sample liquid dilution, reaction, and in situ analysis as described by analysis means 184. This procedure is, of course, repeated as described for each of the sample liquids of interest in turn until sample liquid analyses have been completed.

Under the above circumstances, it will be clear to those skilled in this art that the sample liquid analysis system 180 of FIG. 10 provides all of the heretofore described advantages vis-a-vis the analogous systems of the prior art; and, in combination therewith, provides the additionally significant advantage of completely eliminating the structural and functional requirements of sample liquid stream formation and transport to and through the sample analysis means with minimum carryover.

Figure 11:
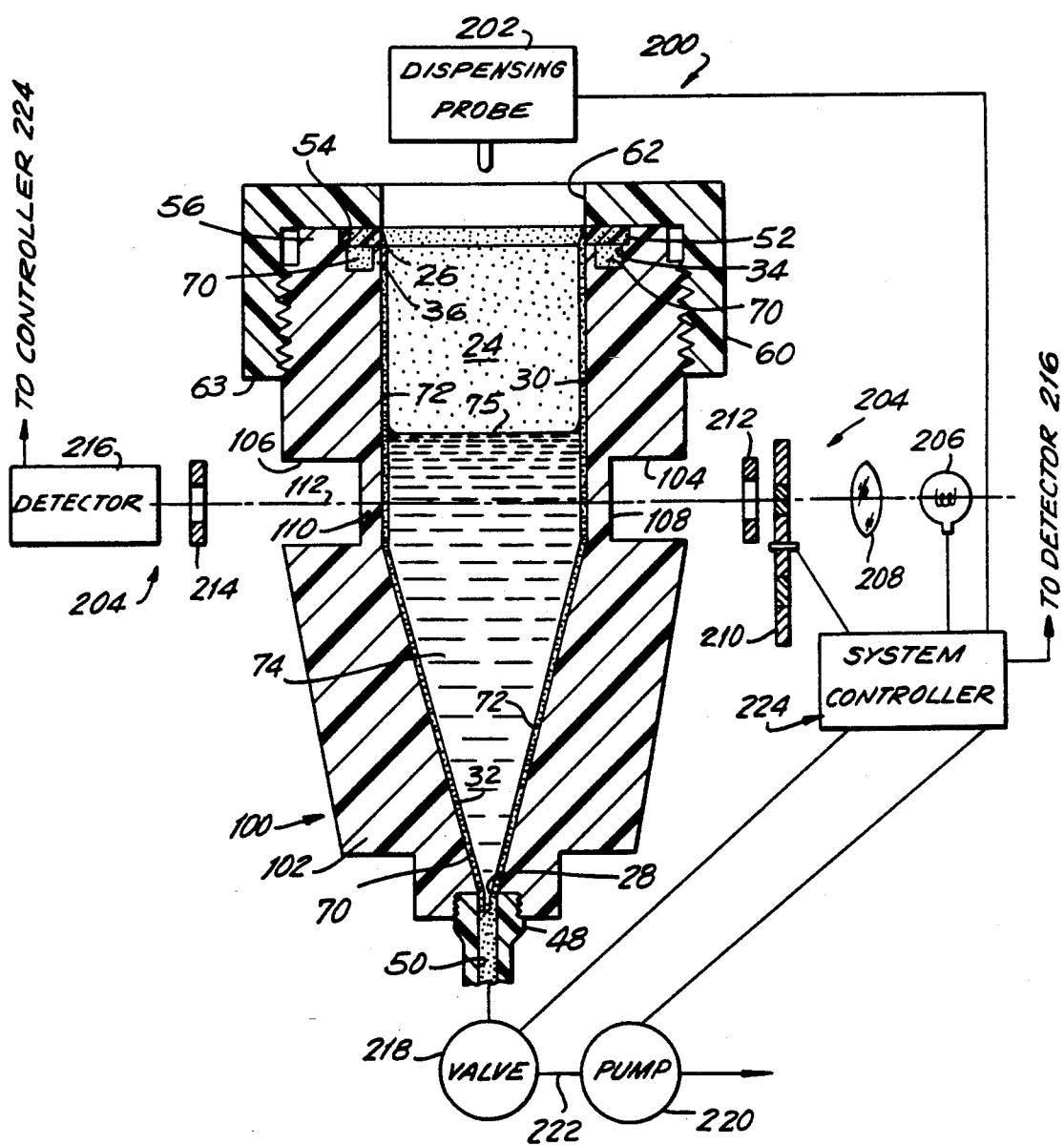
FIG. 11 is an essentially diagrammatic view of a fourth embodiment of a sample analysis system configured and operable in accordance with the teachings of my invention, and includes a cross-sectional view of the container of FIGS. 3 and 4.

A fourth embodiment of a sample analysis system representatively configured and operable in accordance with the teachings of my invention is indicated generally at 200 in FIG. 11, and comprises the minimum carryover container 100 of FIGS. 3 and 4. In this embodiment, container 100 effectively functions as the situs for both sample sample liquid dilution and reaction, and sample liquid analysis, thus again greatly simplifying the sample analysis process by again eliminating the need for sample liquid stream formation and transport, both with minimum sample liquid carryover, to the sample analysis means.

Dispensing probe means, again operable to dispense predetermined quantities of sample, diluent and reagent liquids from respective sources thereof, not shown, into container bore 24, are indicated schematically at 202 in FIG. 11; and may, for example, take the form of the dispensing probe means 122 of FIG. 8, or that of the liquid dispenser with improved probe as disclosed in U.S. Pat. No. 4,121,466.

Sample liquid analysis means taking the form of a colorimeter are schematically indicated at 203 in FIG. 11; and comprise aligned light source 206, lens 208, filter wheel 210, masks 212 and 214, and detector 206 respectively disposed as shown to opposite sides of the container body 102 in alignment with axis 112 of container body bores 108 and 110. This enables the illumination of the relevant portion of a sample liquid 74 at any time in container bore 24 by appropriately processed light energy from light source 206 through light energy-transmittive wall 108; and the detection of that portion of that light energy which passes through the sample liquid 74 and the light energy-transmitting container body wall section 110 to impinge upon detector 216. Since the extent of light energy attenuation by container bore wall sections 108 and 110, and the two relevant layers of the isolation liquid stream 72, will be substantially constant for light energy of fixed intensity and wavelength,,and can be readily determined in each instance, it becomes possible as will be clear to those skilled in this art to quantify the extent of total light energy attenuation attributable to the sample liquid 74 in each instance, thereby effectively colorimetrically analyzing the same.

Valve means and pump means, as respectively schematically depicted at 218 and 220 are operably disposed as shown in a contain body outlet conduit 222 for purposes disclosed hereinabove.

A system controller is indicated schematically at 224 in FIG. 11; and is operatively connected as indicated to each of valve 218, pump 220, light energy source 206, filter wheel 210, dispensing probe means 202, and detector 216 to control and synchronize the respective operations thereof.

With sample analysis system 200 of FIG. 11 configured as described for the automated successive analyses of aqueous sample liquids in situ in container bore 24, it will be clear that with isolation liquid stream 72 independently formed and flowing as described to completely cover the walls of container bore 24 from inlet 26 to outlet 28, and with valve means 218 closed, the respective predetermined quantities of the sample, diluent and reagent liquids for the first sample liquid of interest may be dispensed by dispensing probe means into container bore 24 for dilution and reaction. Once the sample-reagent reaction has been completed, colorimeter 204 is activated to analyze this first diluted and reacted sample liquid of interest. Upon the completion of analysis, valve means 218 are opened, and pump means 220 activated for the complete drainage of the accumulated isolation liquid 70 and the first diluted and reacted sample liquid 74 from the bore 24 for container 100, and the flow thereof to waste, or to other analysis means, not shown, along outlet conduit 222. As sample liquid drainage from bore 24 is completed, valve means 228 are re-closed, and dispensing probe means 202 operated to dispense the respective predetermined quantities of the sample, diluent and reagent liquids of interest for the second sample liquid of interest into container body bore 24 for sample liquid dilution, reaction and analysis as described by colorimeter 204. Operation continues as described for each of the sample liquids of interest in turn until all of the same have been colorimetrically analyzed as described.

Each of the modifications to the container 102 as depicted in FIGS. 6, 7 and 8 may, of course, be employed in the sample analysis system 200 of FIG. 11. With the modification of FIG. 5 which includes the transparent window members 114 and 116 in the container body bores 104 and 106, with resultant reduction in the relevant container body wall sections 108 and 110, greater light energy transmission, and thus greater accuracy for the sample analysis results, would be provided by the analysis system 200. This same advantage would be provided to an even greater extent by the use in system 200 of window members configured as lenses as illustrated at 115 and 117 in FIG. 6 to thereby increase the optical efficiency of colorimetric sample liquid analysis; and would be provided to the maximum extent possible under the described circumstances by the use of the lenses 115 and 117 as the container wall sections in question in the manner illustrated and described with regard to FIG. 7.

By the above is made clear that the sample analysis system 200 again completely eliminates the need for sample liquid stream formation and transport, without additional sample liquid carryover of significance, to the sample analysis means. Thus, a particularly simple, low cost, highly reliable, high speed and accurate, due in large measure to absolute minimization of sample liquid carryover, sample liquid analysis system is provided by analysis system 200 of FIG. 11.

Of course, the container of my invention completely eliminates the need for periodic or inter-sample liquid washing; and is re-usable to a virtually limitless extent since there are no moving parts, and thus nothing to "wear out" as such.

Although a wide range of ratios between the sample, diluent and reagent liquids flow volume, and the flow volume of the isolation liquid, may be employed, a ratio of that nature of 1000/1 is representative.

Carefully monitored and often-repeated precise laboratory testing of the minimum carryover container of my invention has established that the level of whatever minimal amount of carryover that does occur is so low as to be well below contemporary clinical significance.

Of course, the low cost of the hereindisclosed sample liquid analysis systems of my invention renders the paralleling thereof to form multi-channel sample analysis systems most feasible from an economic point of view.

Although disclosed in conjunction with the addition of diluent and reagent liquids to sample liquids for the dilution and reaction of the latter in the container bore, it is clear that this is by way of illustrative example, only, and that the teachings of my invention are by no means limited thereto, but rather, would be equally applicable, for example, to the addition of two or more reagent liquids, either concomitantly or in timed sequence, to each of the sample liquids in question. Too, the container of my invention is, of course, in no way dependent upon the addition of anything to the liquids as are successively contained therein for operation as described. Also, there is no requirement that the sample liquids be aqueous, or that the successively contained liquids be characterizable as "sample liquids.

Various changes may, of course, be made in the hereindisclosed preferred embodiments of my invention without in any way departing from the spirit and scope thereof as defined in the appended claims.

What is claimed is:

1. In an analysis system for the successive analyses of a series of discrete samples liquids with minimum carryover therebetween, the improvements comprising, a container comprising container wall means defining a container bore for the successive containment and processing for analysis of said discrete samples liquids, container bore inlet means for the successive introductions of said discrete sample liquids into said container bore, and container bore outlet means for the successive flows of said discrete liquids from said container bore, means operatively associated with said container bore inlet means for successively introducing said discrete sample liquids into said container bore, said discrete sample liquids introduction means only being operable to introduce a succeeding discrete sample liquid into said container bore after a precedingly introduced discrete sample liquid has flowed completely from said container bore, means operatively associated with said container bore inlet means for introducing at least one discrete sample liquid processing liquid into said container bore for concomitant containment therewithin the each of said discrete sample liquids, and mean independent of said discrete sample liquids and processing liquids introduction means for introducing an isolation liquid which is immiscible with said discrete sample liquids and said processing liquid into said container bore inlet means for flow through said container bore to cover the walls of said container bore from said container bore inlet means to said container bore outlet means with an independently flowing stream of said isolation liquid, said discrete sample liquids and said processing liquids being essentially aqueous liquids, said isolation liquid being a non-aqueous liquid, and said container bore walls being formed by a fluorinated hydrocarbon material which is selectively wettable by non-aqueous liquids to the substantial exclusion of aqueous liquids whereby, contact by said discrete sample liquids and said processing liquids with the walls of said container bore is substantially prevented by said isolation liquid stream to minimize carryover between said discrete sample liquids attendant the successive containment and processing thereof in said container bore.

2. In an analysis system for the successive analyses of a series of discrete liquid samples with minimum carryover therebetween, the improvements comprising, a container comprising container wall means defining a container bore for the successive containment and processing for analysis of said discrete liquids, container bore inlet means for the successive introduction of said discrete liquids into said container bore, and container bore outlet means for the successive flow of said discrete liquids from said container bore, means operatively associated with said container bore inlet means for successively introducing said discrete liquids into said container bore, said discrete liquids introduction means only being operable to introduce a succeeding discrete liquid into said container bore after a precedingly introduced discrete liquid has flowed completely from said container bore, means independent of said discrete liquids introduction means and operatively associated with said container bore inlet means for introducing at least one discrete liquids processing liquid into said container bore for concomitant containment therewithin with each of said discrete liquids and processing of the same within said container bore, and means independent of said discrete liquids and processing liquid introduction means for introducing an isolation liquid which is immiscible with said discrete liquids and said processing liquid into said container bore inlet means for flow through said container bore to cover the walls of said container bore from said container bore inlet means to said container bore outlet means with an independently flowing stream of said isolation liquid, said container bore walls being formed by a material which is selectively wettable by said isolation liquid to the substantial exclusion of said discrete liquids and said processing liquid whereby, contact by said discrete liquids and said processing liquid with the walls of said container bore is substantially prevented by said isolation liquid stream to minimize carryover between said discrete liquids attendant the successive containment and processing thereof in said container bore.

3. In an analysis system as in claim 2 further comprising, outlet passage means operatively connected to said container bore outlet means for the flow of said isolation liquid stream and the successive flow of the processed discrete liquids thereinto form said container bore, and wherein the walls of said outlet passage means are selectively wettable by said isolation liquid to the substantial exclusion of said processed discrete liquids whereby, an isolation liquid based stream of said successively processed discrete liquids will be formed in said outlet passage means, with contact by said processed discrete liquids in said stream with the walls of said outlet passage means being substantially prevented by said isolation liquid to minimize carryover between said processed liquids in said outlet passage means.

4. In an analysis system as in claim 3 further comprising, analysis means operatively associated with said outlet passage means and operable to successively analyze said processed discrete liquids in said processed discrete liquid stream.

5. In an analysis system as in claim 3 further comprising, detector means operatively associated with said outlet passage means and said discrete liquid introduction means, and operable to detect the completion of the flow of each of said discrete liquids in turn from said container bore for the succeeding operation of said discrete liquid introduction means.

6. In an analysis system as in claim 2 further comprising, aligned container bore wall sections disposed to opposite sides of said container bore and being substantially transmittive of light energy whereby, light energy may be transmitted from without said container through processed discrete liquids as contained in said container bore.

7. In an analysis system as in claim 6 further comprising, analysis means which are operable by the transmission and detection of light energy operatively associated with said aligned container bore wall sections, said analysis means being operable to successively analyze said processed discrete liquids in situ in said container bore.

8. In an analysis system as in claim 2 further comprising, analysis means operatively associated with said container and operable to successively analyze said successively contained and processed discrete liquids.

9. In an analysis system as in claim 2 further comprising, means operatively associated with said container bore inlet means and operable to successively withdraw said processed discrete liquids from said container bore inlet means for successive supply to processed discrete liquid analysis means.

10. In an analysis system as in claim 9 further comprising, valve means operatively associated with said container bore outlet means and operable to close the same to prevent the flow of said processed discrete liquids from said container bore.

11. In an analysis system as in claim 2 further comprising, analysis means operatively associated with said container and operable to successively analyze said processed discrete liquids in situ in said container.

12. In an analysis system as in claim 11 further comprising, valve means operatively associated with said container bore outlet means and operable to close the same to prevent the flow of said processed discrete liquids form said container bore.

13. In an analysis system as in claim 11 wherein, said analysis means are immersion analysis means which are successively immersible in said processed discrete liquids in container bore to successively analyze the same.

14. In an analysis system as in claim 13 wherein, said analysis means are an immersion colorimeter.

15. In an analysis system as in claim 13 wherein, said analysis means are immersion electrodes.

16. In an analysis system as in claim 2 wherein, said container bore inlet means are open to atmosphere.

17. In an analysis system as in claim 2 wherein, said isolation liquid introduction means comprise means for introducing said isolation liquid to said container bore inlet means at a first flow rate, said discrete liquid introduction means comprise means for introducing said discrete liquids to said container bore inlet means at a second flow rate, and wherein said first flow rate is significantly lower than said second flow rate.

18. In an analysis system as in claim 2 wherein, said discrete liquid introduction means comprise means for intermittently introducing said discrete liquids into said container bore inlet means, and said isolation liquid introduction means comprise means for continuously introducing said isolation liquid into said container bore inlet means.

19. In an analysis system as in claim 2 wherein, said container bore is generally vertically oriented, said container bore inlet means are above said container bore outlet means, said container bore inlet means are open, and wherein said discrete liquid introduction means comprise dispensing probe means disposed above said container bore inlet means and in alignment therewith, and operable to dispense said discrete liquids directly thereinto.

20. In an analysis system as in claim 19 wherein, said discrete liquid processing liquid introduction means comprise dispensing probe means disposed above said container bore inlet means and in alignment therewith, and operable to dispense said discrete liquid processing liquids directly thereinto.

21. In a container as in claim 2 wherein, said isolation liquid introduction means comprise means for oozing said isolation liquid said container wall means for formation of said independently flowing isolation liquid stream.

22. In an analysis system as in claim 2 wherein, said discrete liquids are aqueous liquids, said isolation liquid is a non-aqueous liquid, and said container bore walls material is one which is selectively wettable by non-aqueous liquids to the substantial exclusion of aqueous liquids.

23. In an analysis system as in claim 22 wherein, said container bore wall material is a fluorinated hydrocarbon, and said isolation liquid is a fluorinated or perfluorinated hydrocarbon.

24. In a container comprising, container wall means defining a container bore for the successive containment of discrete aqueous liquids in said container bore with minimum carryover between said discrete aqueous liquids, container bore inlet means for the successive introductions of discrete aqueous liquids into said container bore by discrete aqueous liquids introduction means, and container bore outlet means for the successive flows of said discrete aqueous liquids from said container bore, the improvements comprising, means operatively associated with said container wall means and independent of said discrete aqueous liquids introduction means for introducing a non-aqueous isolation liquid which is immiscible with said discrete aqueous liquids into said container bore inlet means for flow through said container bore to cover said container bore walls from said container bore inlet means to said container bore outlet means with an independently flowing stream of said isolation liquid, said container bore walls being formed by a fluorinated hydrocarbon material which is selectively wettable by non-aqueous liquids to the substantial exclusion of aqueous liquids and which extends substantially from said container bore inlet means to said container bore outlet means whereby, contact by said successive discrete aqueous liquids with said container bore walls substantially from said container bore inlet means to said container bore outlet means will be substantially prevented by said non-aqueous isolation liquid stream to minimize carryover between said successive discrete aqueous liquids attendant the successive containments thereof in said container bore.

25. In a container comprising, wall means defining a container bore for the successive containment of discrete liquids in said container bore with minimum carryover between said discrete liquids, container bore inlet means for the successive introductions of discrete liquids into said container bore by discrete liquid introduction means, and container bore outlet means for the successive flow of said discrete liquids from said container bore, the improvements comprising, means independent of said discrete liquid introduction means for introducing an isolation liquid which is immiscible with said discrete liquids into said container bore inlet means for flow through said container bore to cover said container bore walls from said container bore inlet means to said container bore outlet means with an independently flowing stream of said isolation liquid, said container bore walls being formed by a material which is selectively wettable by said isolation liquid to the substantial exclusion of said discrete liquids whereby, contact by said discrete liquids with said container bore walls will be substantially prevented by said isolation liquid stream to minimize carryover between said discrete liquids attendant the successive containments of said discrete liquids in said container bore, said isolation liquid introduction means comprising isolation liquid distribution means surrounding said container bore inlet means and operable to uniformly distribute said isolation liquid around said inlet means for uniform flow thereinto to form said isolation liquid stream, said isolation liquid distribution means comprising isolation liquid supply means surrounding said container bore inlet means, and porous means surrounding said container bore inlet means and in communication with said isolation liquid supply means and said container bore inlet means, said porous means being operable to soak up said isolation liquid from said isolation liquid supply means for flow of said isolation liquid from said porous means into said container bore inlet means.

26. In a container as in claim 25 wherein, said container bore is generally vertically oriented, said container bore inlet means are disposed above said container bore outlet means, and said porous means are disposed above said container bore inlet means whereby, said isolation liquid will flow from said porous means into said container bore means under the influence of the force of gravity.

27. In a container as in claim 26 wherein, said isolation liquid supply means comprise a groove surrounding said container bore inlet means and spaced therefrom, and said porous means overlie said groove.

28. In a container as in claim 25 wherein, said porous means are also formed by a material which is selectively wettable by said isolation liquid to the substantial exclusion of said discrete liquids.

29. In a container comprising, container wall means defining a container bore for the successive containment of discrete aqueous liquids in said container bore with minimum carryover between said discrete aqueous liquids, container bore inlet means for the successive introductions of discrete aqueous liquids into said container bore by discrete aqueous liquids introduction means, and container bore outlet means for the successive flow of said discrete aqueous liquids from said container bore, the improvements comprising, means operatively associated with said container wall means and independent of said discrete aqueous liquids introduction mean for introducing a non-aqueous isolation liquid which is immiscible with said discrete aqueous liquids into said container bore inlet means for flow through said container bore to cover said container bore walls from said container bore inlet means to said container bore outlet means with an independently flowing stream of said isolation liquid, said container bore walls being formed by a material which is selectively wettable by non-aqueous liquids to the substantial exclusion of aqueous liquids and which extends substantially form said container bore inlet means to said container bore outlet means whereby, contact by said successive discrete aqueous liquids with said container bore walls substantially from said container bore inlet means to said container bore outlet means will be substantially prevented by said nonaqueous isolation liquid stream to minimize carryover between said successive discrete aqueous liquids attendant the successive containments thereof in said container bore.

30. In a container as in claim 29 wherein, aid container bore is generally vertically oriented, and said inlet means are above said outlet means.

31. In a container as in claim 30 wherein, said container bore inlet means are open, and wherein said discrete liquid introduction means comprise dispensing probe means disposed above said open container bore inlet means and in alignment therewith, and operable to dispense said discrete liquids directly thereinto.

32. In a container as in claim 30 wherein, said isolation liquid introduction means comprise isolation liquid distribution means surrounding said container bore inlet means and operable to uniformly distribute said isolation liquid around said inlet means for uniform flow of the isolation liquid thereinto under the force of gravity to form said isolation liquid stream.

33. In a container as in claim 32 wherein, said isolation liquid distribution means are formed from a material which is selectively wettable by non-aqueous liquids to the substantial exclusion of aqueous liquids.

34. In a container as in claim 29 wherein, said isolation liquid introduction means comprise isolation liquid distribution means surrounding said container bore inlet means and operable to uniformly distribute said isolation liquid around said inlet mean for uniform flow thereinto to form said isolation liquid stream.

35. In a container as in claim 29 further comprising, aligned lens means disposed on opposite sides of said container bore forming portions of the container bore walls whereby, light energy may be transmitted through said container bore from the outside of said container.

36. In a container as in claim 29 further comprising, outlet passage mean operatively connected to said container bore outlet means for the flow of said isolation liquid stream and the successive flows of said discrete aqueous liquids thereinto form said container bore, and wherein the walls of said outlet passage means are formed by a material which is selectively wettable by non-aqueous liquids to the substantial exclusion of aqueous liquids whereby, an isolation liquid-based stream of said successive discrete aqueous liquids will be formed in said outlet passage means, with contact by said discrete aqueous liquids in said stream with the walls of said outlet passage means being substantially prevented by said non-aqueous isolation liquid to minimize carry-over between said discrete aqueous liquids in said outlet passage means.

37. In a container as in claim 36 further comprising, valve means operatively associated with said container bore outlet means and operable to close the same to successively retain said discrete liquids in said container bore.

38. In a container as in claim 29 wherein, said container bore inlet means are open to atmosphere.

39. In a container as in claim 29 wherein, said isolation liquid introduction means comprises means for introducing said isolation liquid to said container bore inlet means at a first flow rate, and said discrete liquid introduction means comprise means for introducing said discrete liquids to said container bore inlet means at a second flow rate, and wherein said first flow rate is significantly lowering than said second flow rate.

40. In a container as in claim 29 wherein, said discrete liquid introduction means comprise means for intermittently introducing said discrete liquids into said container bore inlet means, and said isolation liquid introduction means comprise means for continuously introducing said isolation liquid into said container bore inlet means.

41. In an analysis system as in claim 28 wherein, said isolation liquid introduction means comprises means for oozing said isolation liquid onto said container bore wall means for formation of said independently flowing isolation liquid stream.

* * * * *